United States Patent [19]

Rinehart

[11] 4,059,609

[45] Nov. 22, 1977

[54] S-NAPHTHYL N-ALKYLTHIOLCARBAMATES

[75] Inventor: Jay Kent Rinehart, Akron, Ohio

[73] Assignee: PPG Industries, Inc., Pittsburgh, Pa.

[21] Appl. No.: 693,044

[22] Filed: June 4, 1976

[51] Int. Cl.$^2$ .......................................... C07C 155/02
[52] U.S. Cl. .................................. 260/455 A; 71/100; 424/300
[58] Field of Search .................................. 260/455 A

[56] References Cited

PUBLICATIONS

J. Amer. Chem. Soc. vol. 31, (1966), pp. 3980–3984.

*Primary Examiner*—Delbert R. Phillips
*Attorney, Agent, or Firm*—Robert J. Grassi

[57] ABSTRACT

S-naphthyl N-alkylthiolcarbamates, such as S-α-naphthyl N-methylthiolcarbamate, and S-β-naphthyl N-methylthiolcarbamate and S-α-naphthyl N,N-dimethylthiolcarbamate are disclosed. These are useful for controlling plant pests such as weeds, pathogenic nematodes, fungi, or other pathogenic organisms. Also disclosed are methods of controlling plant pests with these compounds.

12 Claims, No Drawings

S-NAPHTHYL N-ALKYLTHIOLCARBAMATES

BACKGROUND OF THE INVENTION

This invention concerns S-naphthyl N-alkylthiolcarbamates, particularly those in which the alkyl has up to five carbon atoms. This invention also concerns methods of controlling plant pests with these compounds.

DESCRIPTION OF THE PRIOR ART

Plant pests such as weeds, nematodes, fungi, bacteria, insects, virus and other microorganisms continually affect the growth of crops, trees, and other desirable vegetation. One method of controlling plant pests is by application of chemicals which affect the plant pests. These chemicals are applied to the soil, to the desirable plant, or directly to the plant pest itself. Because millions of plant pests exist and differ in tolerance to chemicals, new chemicals must be discovered which are effective to control the deleterious effects of plant pests. Especially desirable are chemicals which have activity against a broad spectrum of plant pests.

The prior art claims that certain thiolcarbamates are effective against plant pests. The following patents and references describe these thiolcarbamates and the plant pests against which they are effective.

U.S. Pat. Nos. 2,977,209 and 3,265,563 disclose S-phenyl N-alkylthiolcarbamates, S-chlorophenyl N-alkylthiolcarbamates, S-ethoxyphenyl N-allylthiolcarbamate, S-ethoxyphenyl N-alkylthiolcarbamates, S-p-tolyl N-alkylthiolcarbamates, and S-2,4-dimethylphenyl N-alkylthiolcarbamates as herbicides and fungicides. U.S. Pat. No. 2,992,332 discloses S-4-methylbenzyl-N,N-diethylthiocarbamate as a herbicide for rice fields. U.S. Pat. No. 3,301,885 discloses S-substituted phenyl N-alkyl, N-alkoxy thiolcarbamates as herbicides, miticides, and insecticides. U.S. Pat. No. 3,687,653 discloses trifluoromethylbenzyl N-alkylthiolcarbamates as herbicides. U.S. Pat. No. 3,046,189 and Canadian Pat. No. 789,575 discloses S-alkyl N-alkylthiocarbamates as nematocides. R. Reimschneider and O. Lorenz, in *Monstsch.*, 84, 518 (1953) describe S-phenyl N,N-dimethylthiolcarbamate, and D. G. Crosby and C. Niemann, *Journal of American Chemical Society*, 76, 4458 (1954) describe S-phenyl N-cyclohexylthiolcarbamate, and S-phenyl N-phenylthiolcarbamate. Netherland Pat. No. 6,606,753 discloses S-phenyl N-trifluoromethylphenylthiocarbamate and S-substituted phenyl N-substituted trifluoromethylphenylthiocarbamates as anthelmintics. M. S. Newman and H. A. Karnes *Journal of Organic Chemistry*, 31, 3980-3983 describe S-β-naphthyl N,N-dimethylthiolcarbamate, S-2-nitrophenyl N,N-dimethylthiolcarbamate. S-3-nitrophenyl N,N-dimethylthiolcarbamate, S-2,4,5-trichlorophenyl N,N-dimethylthiolcarbamate, S-3-trifluoromethylphenyl N,N-dimethylthiolcarbamate, S-2,3,5,6-tetramethylpentyl N,N-dimethylthiolcarbamate, S-4-tert-butylphenyl N,N-dimethylthiolcarbamate, S-2-methoxyphenyl N,N-dimethylthiolcarbamate and S-4-methoxyphenyl N,N-dimethylthiocarbamate.

SUMMARY OF THE INVENTION

This invention concerns biologically active, agriculturally useful novel S-naphthyl N-alkylthiolcarbamates of S-α-naphthyl N-alkylthiolcarbamates of the general formula:

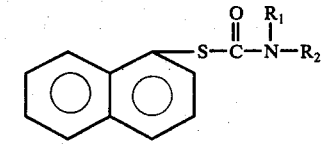

wherein:
$R_1$ is H, or an alkyl of from one to five carbon atoms, and
$R_2$ is an alkyl of from one to five carbon atoms, and S-β-naphthyl N-alkylthiolcarbamates of the general formula:

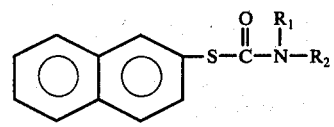

wherein:
$R_1$ is hydrogen or an alkyl of from one to five carbon atoms, (S-β-naphthyl N,N-dimethylthiolcarbamate is known) and
$R_2$ is an alkyl of up to five carbon atoms, some of which are novel.

It also concerns the method of using both these compounds and known compounds to control either the plant pests, or their deleterious effects, or both the plant pests and their deleterious effects, particularly nematodes of Meloidogyne, weeds, bacteria, fungi, and related microorganisms.

DESCRIPTION OF THE PREFERRED EMBODIMENTS

The S-α-naphthyl N-alkylthiolcarbamates of this invention are represented by the following general formula:

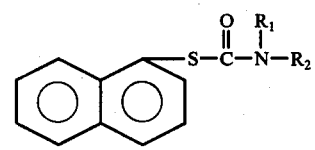

wherein:
$R_1$ is hydrogen, or an alkyl of from one to five carbon atoms, and
$R_2$ is an alkyl of one to five carbon atoms.

The S-β-naphthyl N-alkylthiolcarbamates of this invention are represented by the general formula:

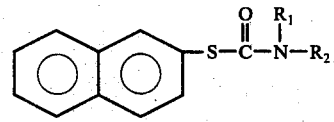

wherein:
$R_1$ and $R_2$ are as described before.

The phrase "alkyl of one to five carbon atoms" includes the following straight chain alkyls and branched chain alkyls:

methyl, ethyl, propyl, isopropyl, n-butyl, sec-butyl, isobutyl, tert-butyl, pentyl, 1-methylbutyl, 1-ethylpropyl, isopentyl, 1-isopropylethyl, neopentyl, and tert-pentyl.

Preferred are the S-naphthyl N-alkylthiolcarbamates having straight chain alkyls of methyl, ethyl, n-propyl, n-butyl, and pentyl. Those in which the alkyl group is methyl, ethyl, and n-propyl are especially preferred with the methyl compounds being most preferred.

Specific S-naphthyl N-alkylthiolcarbamates contemplated by this invention include those of the general formulas in which $R_1$ is hydrogen and $R_2$ is an alkyl of from one to five carbon atoms; representative compounds are:

S-$\beta$-naphthyl N-methylthiolcarbamate;
S-$\beta$-naphthyl N-ethylthiolcarbamate;
S-$\beta$-naphthyl N-propylthiolcarbamate;
S-$\beta$-naphthyl N-isopropylthiolcarbamate;
S-$\beta$-naphthyl N-n-butylthiolcarbamate;
S-$\beta$-naphthyl N-sec-butylthiolcarbamate;
S-$\beta$-naphthyl N-isobutylthiolcarbamate;
S-$\beta$-naphthyl N-tert-butylthiolcarbamate;
S-$\beta$-naphthyl N-pentylthiolcarbamate;
S-$\beta$-naphthyl N-1-methylbutylthiolcarbamate;
S-$\beta$-naphthyl N-1-ethylpropylthiolcarbamate;
S-$\beta$-naphthyl N-1-isopentylthiolcarbamate;
S-$\beta$-naphthyl N-1-neopentylthiolcarbamate; and
S-$\beta$-naphthyl N-tert-pentylthiolcarbamate.
S-$\alpha$-naphthyl N-methylthiolcarbamate;
S-$\alpha$-naphthyl N-ethylthiolcarbamate;
S-$\alpha$-naphthyl N-propylthiolcarbamate;
S-$\alpha$-naphthyl N-isopropylthiolcarbamate;
S-$\alpha$-naphthyl N-n-butylthiolcarbamate;
S-$\alpha$-naphthyl N-sec-butylthiolcarbamate;
S-$\alpha$-naphthyl N-isobutylthiolcarbamate;
S-$\alpha$-naphthyl N-tert-butylthiolcarbamate;
S-$\alpha$-naphthyl N-pentylthiolcarbamate;
S-$\alpha$-naphthyl N-1-methylbutylthiolcarbamate;
S-$\alpha$-naphthyl N-1-ethylbutylthiolcarbamate;
S-$\alpha$-naphthyl N-isopentylthiolcarbamate;
S-$\alpha$-naphthyl N-neopentylthiolcarbamate; and
S-$\alpha$-naphthyl N-tert-pentylthiolcarbamate.

Preferably, $R_2$ is a straight chain alkyl mentioned herein.

Other compounds include those of the general formulas in which $R_1$ is an alkyl of one to five carbon atoms, and $R_2$ is an alkyl of two to five carbon atoms, representative compounds of which are:

S-$\alpha$-naphthyl N,N-di(tert-butyl)thiolcarbamate;
S-$\alpha$-naphthyl N-sec-butyl-N-neopentylthiolcarbamate;
S-$\alpha$-naphthyl N-isopropyl-N-1-methylbutylthiolcarbamate;
S-$\beta$-naphthyl N-isopentyl-N-1-ethylpropylthiolcarbamate; and
S-$\beta$-naphthyl N-isobutyl-N-tert-pentylthiolcarbamate.

Of those compounds of the general formulas wherein $R_1$ and $R_2$ are one to five carbon alkyls, the preferred compounds are those in which $R_1$ is a straight chain alkyl, notably methyl, and $R_2$ is a branched alkyl, representative compounds of which are:

S-$\alpha$-naphthyl N-pentyl-N-sec-butylthiolcarbamate;
S-$\beta$-naphthyl N-n-butyl-N-isopentylthiolcarbamate;
S-$\alpha$-naphthyl N-methyl-N-sec-butylthiolcarbamate; and
S-$\beta$-naphthyl N-methyl-N-neopentylthiolcarbamate.

Another group of preferred S-naphthyl N-methyl-N-lower alkylthiolcarbamates are those in which the lower alkyl is a one to five carbon straight chain alkyl such as:

S-$\alpha$-naphthyl N,N-dimethylthiolcarbamate;
S-$\alpha$-naphthyl N-methyl-N-ethylthiolcarbamate;
S-$\alpha$-naphthyl N-methyl-N-propylthiolcarbamate;
S-$\alpha$-naphthyl N-methyl-N-n-butylthiolcarbamate;
S-$\alpha$-naphthyl N-methyl-N-pentylthiolcarbamate;
S-$\beta$-naphthyl N,N-dimethylthiolcarbamate;
S-$\beta$-naphthyl N-methyl-N-ethylthiolcarbamate;
S-$\beta$-naphthyl N-methyl-N-propylthiolcarbamate;
S-$\beta$-naphthyl N-methyl-N-n-butylthiolcarbamate; and
S-$\beta$-naphthyl N-methyl-N-pentylthiolcarbamate.

Also, compounds in which both $R_1$ and $R_2$ are straight chain alkyls mentioned herein are very useful, representative of such compounds are:

S-$\beta$-naphthyl N,N-di(propyl)thiolcarbamate and
S-$\alpha$-naphthyl N-ethyl-N-pentylthiolcarbamate.

NOVEL COMPOUNDS

Those S-$\alpha$-naphthyl N-alkylthiolcarbamate compounds of the general formula:

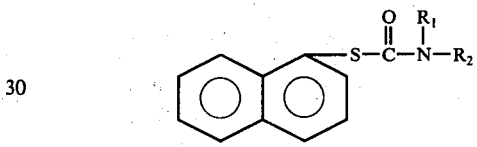

wherein:
$R_1$ is hydrogen, or an alkyl having from one to five carbon atoms, and
$R_2$ is an alkyl having from one to five carbon atoms are believed to be novel.

Those S-$\beta$-naphthyl N-alkylthiolcarbamates of the general formula:

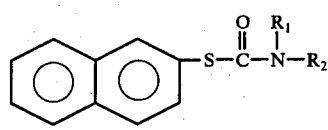

wherein:
$R_1$ is hydrogen, or an alkyl of from two to five carbon atoms, and
$R_2$ is an alkyl of from one to five carbon atoms are believed to be novel. The S-$\beta$-naphthyl N,N-dimethylthiolcarbamate is known (*Journal of Organic Chemistry*, 31, pages 3980–3983).

The following Examples I and II illustrate the synthesis of certain of these compounds by the reaction of $\alpha$- or $\beta$-naphthalenethiol with alkyl isocyanates having an alkyl mentioned herein.

EXAMPLE I

S-$\beta$-naphthyl N-methylthiolcarbamate

Methyl isocyanate (2.7 grams, 47 millimoles) in anhydrous ethyl ether (10 milliliters) was slowly added (20 minutes) to a stirred mixture of $\beta$-naphthalenethiol (7.2 grams, 45 millimoles) and one to two drops of triethylamine in anhydrous ethyl ether (50 milliliters). The clear reaction mixture was refluxed for 4 hours, and the ethyl ether solvent was allowed to evaporate off.

A crystalline material was obtained (9.7 grams) (99 percent yield) which was recrystallized from benzene (100 milliliters) to produce 7.6 grams of a crystalline S-β-naphthyl N-methylthiolcarbamate product having a melting point of 105°–106° Centigrade and an infrared spectrum (using the split mull technique) with a N—H band at 3340 centimeters$^{-1}$, and a C=O band at 1650 centimeters$^{-1}$.

Analysis for: $C_{12}H_{11}NOS$; Calculated percentage: C, 66.33; H, 5.10; N, 6.45; Found (Combustion Analysis) Percentage: C, 66.75, 66.45; H, 4.99, 4.95; N, 6.26, 6.23

EXAMPLE II

S-α-naphthyl N-methylthiolcarbamate

The procedure of Example I was followed using 2.0 grams (12.5 millimoles) of α-naphthalenethiol and 0.8 grams (14 millimoles) of methylisocyanate to obtain 2.5 grams (93 percent yield) of a crystalline S-α-naphthyl N-methylthiolcarbamate product which was not recrystallized and which had a melting point of 129°–133° Centigrade, and an infrared spectrum with a N—H band at 3280 centimeters$^{-1}$ and a C=O band at 1650 centimeters$^{-1}$.

Solvents other than ethyl ether such as benzene, tetrahydrofuran, may be used for conducting the synthesis of the compounds.

Alternatively, the compounds of this invention may be prepared by reacting alkylamines or dialkylamines having the alkyl mentioned herein with S-α-naphthylthiolchloroformate, or S-β-naphthylthiolchloroformate (formed and described in U.S. Pat. No. 3,165,544) in the presence of a stoichiometric amount of an acid (hydrogen chloride) acceptor such as sodium hydroxide, pyridine, alkyl substituted pyridines, trialkylamines and potassium hydroxide.

This chloroformate method of synthesis of the thiolcarbamates is conducted as follows:

A solution containing about 45 millimoles of the appropriate naphthalene thiolchloroformate in about 10 to 20 milliliters of ethyl ether, or other solvent mentioned herein, is added dropwise over a 20 minute period, to a vigorously stirred amine solution containing about 100 milliliters of water, 100 milliliters of ethyl ether, 45 millimoles of the appropriate alkylamine or dialkylamine having an alkyl mentioned herein, and 45 millimoles (a stoichiometric amount) of an acid acceptor such as trialkylamine or dimethylaniline, or N-methyl morpholine or other acid acceptor mentioned herein. This reaction is conducted in equipment having a reflux condenser and the temperature range is from 0° to the refluxing temperature (about 34° to 1 atmosphere pressure with ethyl ether) with 20° C. to the reflux temperature being preferred. After the addition of the appropriate naphthalene thiolchloroformate is complete, the reaction mixture is stirred for an additional period of time of about 0.5 to 2.0 hours.

The layers of the solution are separated; the aqueous layer is washed with about 100 milliliters of ethyl ether, and this ethyl ether washing and the ethyl ether layer of the solution are combined and washed with 100 milliliters of aqueous solutions of 10 weight percent of sodium hydroxide, and 10 weight percent hydrochloric acid, respectively, and then are dried with anhydrous sodium sulfate ($Na_2SO_4$). After filtering off the sodium sulfate, the ethyl ether, or other appropriate solvent mentioned herein, is removed such as by evaporation with a rotary evaporator. Generally the product will precipitate out during removal of the solvent, and then can be recrystallized; otherwise the product remaining when most of the solvent is removed may itself be used, for the purposes mentioned herein.

Yet another reaction which may be utilized to prepare the contemplated compounds is to react alkyl amines or dialkylamines with phosgene to form the corresponding alkylcarbamoyls, or dialkylcarbamoyls which upon reaction with α or β naphthalenethiols mentioned herein yield the S-napthyl N-alkylthiolcarbamates illustrated above.

The following examples illustrate the synthesis of the compounds disclosed herein by reaction of a naphthalenethiol with an alkyl or dialkylcarbamoyl chloride.

EXAMPLE III

S-β-naphthyl N,N-dimethylthiolcarbamate

A 5 milliliter anhydrous ethyl ether solution of dimethylcarbamoyl chloride (4.8 grams, 45 millimoles; redistilled) and a 5 milliliter anhydrous ethyl ether solution of triethylamine (4.6 grams, 45 millimoles) were simultaneously added over a 40 minute period at ambient temperature to a stirred 40 milliliter anhydrous ethyl ether solution of S-β-napthalenethiol (7.2 grams, 45 millimoles). The reaction mixture was stirred and refluxed for 2 ½ hours and cooled to room temperature and then poured in 100 milliliters of distilled water. The organic layer and aqueous layer were separated, and the aqueous layer was extracted with ethyl ether, which extracts were combined with the organic layer. The combined ether extracts and organic layer were washed with 100 millimeters of a 10 weight percent aqueous solution of sodium hydroxide (NaOH), then with 100 milliliters of a 10 weight percent aqueous hydrochloric acid solution, and then dried with sodium sulfate ($Na_2SO_4$) and filtered.

The solvent was removed on a rotary evaporator to give 8.5 grams (82 percent yield) of a crude product, which crystallized upon cooling. It was recrystallized from benzene to give 4.1 grams of crystalline S-β-naphthyl N,N-dimethylthiolcarbamate product, having an infrared spectrum with a C=O band at 1660 centimeters$^{-1}$, and a melting point of 97.5°–105° Centigrade.

EXAMPLE IV

S-α-naphthyl N,N-dimethylthiolcarbamate

The procedure of Example III was followed using 3.4 grams (21 millimoles) of α-naphthalenethiol, 2.2 grams (21 millimoles) of triethylamine, and 2.3 grams (21 millimoles) of dimethylcarbamoyl chloride to obtain 3.4 grams (69.5 percent yield) of a liquid product containing S-α-naphthyl N,N-dimethylthiolcarbamate which did not crystallize. The product was 96 percent pure as calculated by its NMR spectra, and it had an infrared spectrum with a C=O band at 1660 centimeters$^{-1}$.

Removal of the solvents, and reactants or other impurities from the S-napthyl N-alkylthiolcarbamates mentioned herein is only necessary when their presence would interfere with the intended use of the compounds, such as their use for systemic control of nematodes. All conventional purification techniques; such as recrystallization from solvents, fractional crystallization, washing with one or more solvents, followed by evaporation of the solvents, or filtration from the solvents; or their equivalents may be used.

PROPERTIES

The S-naphthyl N-alkylthiolcarbamates of this invention possess one or more properties which make them useful for agricultural applications to control plant pests, or the deleterious effects of plant pests, or both plant pests and their deleterious effects. Such properties are: the ability to systemically control the harmful effects of nematodes particularly root knot nematodes, the ability to control pathogenic nematodes by direct contact or by incorporation of the compound into soil prior to or after infestation with nematodes, the ability to control diseases caused by certain pathogenic fungi or other microorganisms, the ability to control insects, or the ability to control weeds (undesirable plants).

These useful properties of the compounds disclosed herein are illustrated by the following examples of laboratory or greenhouse tests.

SYSTEMIC NEMATODE CONTROL TESTS

EXAMPLES V to XIX

This test illustrates systemic control of the deleterious effect of nematodes upon plants, particularly, those growing in soil infested with pathogenic nematodes which cause root knots.

Systemic control as used herein refers to the ability of a compound to control the adverse effect of nematodes on plants by application of the compounds to the foliage of a plant, without the compound harming the plant, that is without phytotoxic, or herbicidal effects upon the plant, at the concentration used for systemic control.

In the test procedure for the test examples a stock acetone solution consisting of 99.75 weight percent of acetone, 0.20 percent sorbitan trioleate (Span 85) and 0.05 percent sorbitan monooleate polyoxyalkylene derivative (Tween 80) was used. The test compound was dissolved in an aliquot of the stock solution, and deionized water was added to form the desired concentration for spraying. For example, 1200 mg. of S-α-naphthyl N-methylthiolcarbamate was dissolved in 80 grams of the stock acetone solution, and this solution was diluted to 1,000 grams to form a spray solution containing 1200 ppm of S-α-naphthyl N-methylthiolcarbamate.

Bonny Best tomato plants were grown from seedlings for 4 or 5 weeks in sterile soil until their height was 6 to 8 inches, and the plants had at least three fully expanded leaves (usually more).

Such growing tomato plants were separated into two groups, one for spray treatment (treated) and the other to serve as the control. The plants being treated were passed through a spraying machine which sprayed them with the previously prepared test solution. The control group was not sprayed.

The solution of the test compound, i.e., S-α-naphthyl N-methylthiolcarbamate was applied as a spray by passing a tray of pots containing tomato plants, under a sprayer equipped with a Tee-jet 8001 E spray nozzle tip and operating in the range of 35–40 pounds per square inch of pressure. The pot containing the plant was loaded within a tray which was placed on a conveyor belt moving at about 0.0625 mph (5.49 feet per minute). When the tray passed under the spray head, it tripped a microswitch which operated the sprayer. The spray was applied to the dripping point. The amount of compound within the solvent was adjusted to give the required application rate expressed as parts per million (ppm) for the active ingredient per 30 milliliters of solution or pounds of active ingredient per 200 gallons per surface acre (lbs. ai/200 gal/acre) of soil. In these examples the sprayer sprayed 30 milliliters of solution per replicate. The sprayed plants were dried; then they and the control plants were transferred into soil infested with root-knot nematodes (Meloidogyne incognita), and grown under greenhouse conditions using natural sunlight, with an average temperature of 60°–70° Fahrenheit in the winter and 70°–80° Fahrenheit in the summer.

Both the sprayed (treated) and control plants were uprooted 4 weeks after being transferred to the infested soil, and their roots were examined for root-knots which were counted in accordance with the method of W. M. Zeck. Pflanzenschutz - Nachrichten, Vol. 24, pages 141–144 (1971). The control was also rated according to the Zeck index. The root-knot counts were related to percent control by the following formula:

$$\% \text{ control} = 100\% - \frac{(\text{number of root knots in treated plants})}{(\text{number of root knots in the control plants})} (100\%)$$

Vydate (Dupont 1410 - methyl N',N'-dimethyl-N-[(methylcarbamoyl)oxy]-1-thioxamimidate) a systemic nematocide known to be effective against the root-knot nematodes was also tested at the same concentration as the test compound and under the same conditions, as an internal check in some examples. Treated plants were also observed for evidence of damage by the applied test compound, which is reported on the same herbicidal scale mentioned herein under herbicidal tests.

Five replicates per concentration of the test compound were made and an average percent control was determined based on these five replicates. Each replicate was based on two plants. An average value of 10 or higher indicates systemic control of the deleterious effects of nematodes on the test plants.

Test results obtained from these tests are shown in Table 1. Column 1 gives the example number of the test; column 2 gives the test compound used, unless indicated otherwise, the sample was prepared as described herein; column 3 gives the concentration (conc.) of test compound applied expressed as parts per million (ppm) as well as that of the check compound Vydate; column 4 gives the individual percent control per replicate for test compound at the indicated concentration; column 5 gives the indicated concentration; and column 6 gives the average Zeck index rating of the control plants. The Zeck index indicates the extent of the nematode activity during the test. The greater the value the more extensive is the nematode activity during the test.

TABLE 1

| SYSTEMIC CONTROL OF ROOT-KNOT NEMATODE, (Meloidogyne incognita) UPON TOMATO PLANTS | | | | | | | | | | | | | |
|---|---|---|---|---|---|---|---|---|---|---|---|---|---|
| Example No. | Compound Applied (2) | Conc. ppm | Percent Control-Replicate | | | | | Check Compound-Vydate Percent Control-Replicate | | | | | Zeck Index Rating |
| | | | 1 | 2 | 3 | 4 | 5 | 1 | 2 | 3 | 4 | 5 | |
| V | S-α-naphthyl N-methyl-thiolcarbamate | 500 | 18 | 34 | 34 | 18 | 34 | 67 | 51 | 51 | 67 | 67 | 6.1 |

TABLE 1-continued
SYSTEMIC CONTROL OF ROOT-KNOT NEMATODE, (Meloidogyne incognita)
UPON TOMATO PLANTS

| Example No. | Compound Applied (2) | Conc. ppm | Percent Control-Replicate | | | | | Check Compound-Vydate Percent Control-Replicate | | | | | Zeck Index Rating |
|---|---|---|---|---|---|---|---|---|---|---|---|---|---|
| | | | 1 | 2 | 3 | 4 | 5 | 1 | 2 | 3 | 4 | 5 | |
| VI | " | 50 | 34 | 51 | 34 | 34 | 51 | 51 | 51 | 67 | 34 | 51 | 6.1 |
| VII | " | 5 | 18 | 34 | 34 | 34 | 18 | 34 | 51 | 51 | 34 | 51 | 6.1 |
| VIII | S-β-naphthyl N-methyl-thiolcarbamate | 500 | 18 | 34 | 51 | 51 | 51 | 67 | 51 | 51 | 67 | 67 | 6.1 |
| IX | " | 50 | 51 | 51 | 51 | 67 | 67 | 51 | 51 | 67 | 34 | 51 | 6.1 |
| X | " | 5 | 51 | 67 | 67 | 51 | 67 | 34 | 51 | 51 | 34 | 51 | 6.1 |
| XI | S-phenyl N-methyl-thiolcarbamate (3) | 500 | 51 | 51 | 34 | 67 | 51 | 67 | 51 | 51 | 67 | 67 | 6.1 |
| XII | " | 50 | 51 | 51 | 51 | 51 | 51 | 51 | 51 | 67 | 34 | 51 | 6.1 |
| XIII | " | 5 | 34 | 51 | 34 | 51 | 51 | 34 | 51 | 51 | 34 | 51 | 6.1 |
| XIV | S-phenyl N-ethyl-thiolcarbamate (3) | 500 | 60 | 75 | 55 | 55 | 60 | 77 | 47 | 75 | 62 | 62 | a |
| V (1) | " | 50 | 32 | 44 | 75 | 60 | 80 | 32 | 27 | 75 | 62 | 70 | b |
| XVI | " | 5 | 70 | 0 | 0 | 0 | 62 | 15 | 75 | 50 | 0 | 0 | c |
| XVII | S-phenyl N-butyl-thiolcarbamate (3) | 500 | 50 | 35 | 37 | 100 | 70 | 77 | 47 | 75 | 62 | 62 | a |
| XVIII | " | 50 | 60 | 75 | 50 | 0 | 87 | 32 | 27 | 75 | 62 | 70 | b |
| XIX | " | 5 | 60 | 0 | 80 | 27 | 52 | 15 | 75 | 50 | 0, | 0--; | c |

(1) This compound gave a trace burn which the plant outgrew. Herbicidal rating of 1B; all other compounds tested had no effect upon the plants at the concentration at which the compounds were tested.
(2) Unless otherwise indicated, these test compounds are those formed by the synthesis described herein.
(3) Described in U.S. Pat. No. 2,977,209 and U.S. Pat. No. 3,265,563 and disclosed as a systemic nematocide in Applicant's copending application entitled SYSTEMIC NEMATOCIDES, Serial No. 408,775, filed October 23, 1973.
a The average number of knots for the untreated plants was 55 ± 6 knots (low Zeck rating).
b The average number of root knots for the untreated plants was 53 ± 7 knots.
c The average number of root knots for the untreated plants was 40 ± 13 knots.

TEST FOR SOIL CONTROL OF NEMATODES

EXAMPLES XX to XXVI

This test shows whether the test compound (when incorporated into the soil) affects the nematodes' deleterious effect on the plant.

PROCEDURE

The test compound was added to a sample of soil infested with *Meloidogyne incognita,* and thoroughly blended therein. The chemically treated soil sample was sealed in a plastic bag and stored at 68°-70° Fahrenheit for 2 weeks.

The soil was removed from the bag, potted, seeded with Bonny Best Tomato seed, and watered (treated samples). The amount of test compound used is stated as pounds per acre, and is based on a 6 inch depth of soil.

A sample of infested soil which has not been treated with the test compound was also potted, seeded with Bonny Best Tomato seed, and watered (control samples).

The treated, control, and internal check samples were placed in a greenhouse about 18 days to allow for the germination of the seeds and growth of the plants. The plants were uprooted, the root knots were counted and the percent control was calculated as described herein for the Systemic Nematode Control Test.

The results of these tests are shown in Table 2. Column 1 of Table 2 lists the example number; column 2 lists the compound tested; column 3 gives the test results, at an application rate of 50 pounds of the compound per acre per 6 inch depth of soil. In some examples, results are shown for repeated tests as well as at different application rates. The test compounds used were synthesized as described herein. "0" percent means no control of the deleterious effect of nematodes on plants, "100" percent means complete control of the deleterious effects of the nematodes upon the plants.

TABLE 2
TEST RESULTS FOR SOIL CONTROL OF NEMATODES
OF Meloidogyne incognita

| Example No. | Compound | Percent Control At (Pounds Per Acre) | | | |
|---|---|---|---|---|---|
| | | 50 | 25 | 12 | 6 |
| XX | S-β-naphthyl N-methyl-thiolcarbamate | 93 | NT | NT | NT |
| XXI | S-β-naphthyl N,N-dimethyl thiolcarbamate[c] | 0 | NT | NT | NT |
| XXII | S-α-naphthyl N,N-dimethyl-thiolcarbamate | 0 | NT | NT | NT |
| XXIII | S-α-naphthyl N-methyl-thiolcarbamate | 0 | NT | NT | NT |
| XXIV | S-phenyl N-methyl-thiolcarbamate[a] | 88, | 98, | 84, | 80, |
| | | NT, | 83, | 69, | 56, |
| | | NT, | 0, | 0, | 0, |
| | | NT, | 96, | 100, | 83, |
| | | 80[b], | NT, | NT, | NT, |
| | | NT | 75 | 54 | 36 |
| XXV | S-phenyl N-ethyl-thiolcarbamate[a] | NT, | 0 | 0 | 0 |
| | | 52 | NT | NT | NT |
| XXVI | S-phenyl N-n-butyl-thiolcarbamate[a] | NT, | 0 | 0 | 0 |
| | | 72 | NT | NT | NT |

[a] known compound, see U.S. 2,977,209 and U.S. 3,265,563, and also disclosed as a systemic nematocide in Applicant's copending application SYSTEMIC NEMATOCIDES, Serial No. 408,775, filed October 23, 1973.
[b] herbicidal effect on plants rating 3:R.
[c] known compound, M. S. Newman and H. A. Karnes, Journal of Organic Chemistry, 31, page 3980.
NT not tested for this test series.

SOIL FUNGICIDAL TESTS

EXAMPLES XXVII to XXVIV

These fungicidal tests indicate if the test compound protects against the deleterious effects of one or more soil fungi.

The specific tests are for the disease causing fungi of *Sclerotium rolfsii* (Stem Rot of Peanuts), *Pythium ultimum* (Damping Off), *Rhizoctonia solani* (Damping Off), and *Fusarium solani* (Bean Root Rot), or Fusarium Wilt of Tomatoes.

TEST PROCEDURE FOR *Sclerotium rolfsii*

A blend of sterile soil and sclerotia of *Sclerotium rolfsii* was made, and a blend of sterile soil and the test compound (normally added to the soil as a solution) was made. Then the chemically treated soil was added to an equivalent weight of the Sclerotium-inoculated soil, and the mixture placed in a blender and thoroughly blended. This blend was then equally divided, and each division was placed in a container, implanted with two carrot slices, water sealed, then placed in a greenhouse operated at 70°-80° Fahrenheit temperature, and a humidity range of 50-95 percent, for 4-5 days, and observed for infection growth. The final observation (treated samples) is made after the fifth day in the greenhouse. Containers of sterile soil only, sterile soil plus chemical, sterile soil plus *Sclerotium inoculum* (control) were also implanted with carrot slices, and incubated under the same conditions as the treated samples.

Control effectiveness of a test compound was determined by comparing the actual count of infection loci on carrot slices in soil chemically treated with the test compound, with the actual count of infection loci on carrot slices in Sclerotium-inoculated soil.

The severity of the disease was determined by comparing the actual count of infection loci on carrot slices in Sclerotium-inoculated soil with the actual count of infection loci on carrot slices in sterile soil.

Each test is based on a minimum of three replicates. The amount of test compound is expressed as pounds per acre (lb/A) for a 6 inch depth of soil. Generally the weight of Sclerotium used per dry weight of soil was 8 grams of Sclerotium (over winter stage) per 3,000 milliliters of dry soil.

Control effectiveness is expressed as percent control and was calculated by the following formula:

$$\% \text{ control} = 100\% - \frac{(\text{number of infection loci in treated carrots})}{(\text{number of infection loci in control carrots})} \cdot 100\%$$

TEST PROCEDURE FOR *Pythium ultimum*

Oospores suspensions of *Pythium ultimum* which have been examined with a haemocytometer for oospore (plus chlamydospore) numbers per milliliter, were blended with dry sterilized soil.

A blend of sterile soil and the test compound (normally added to the soil as a solution) was also made. The chemically treated soil was mixed with the Pythium-inoculated soil and thoroughly mixed in a soil blender, and the mixture was equally divided, and division was placed into a container seeded with sugar beet seeds, water sealed, and placed in a greenhouse, maintained at 50-75 percent humidity, and 70°-80° Fahrenheit, for 2 weeks.

Containers of sterile soil only, sterile soil plus the test compound, and steril soil plus *Pythium inoculum*, were also seeded with sugar beet seeds and placed in the greenhouse.

Observations were made for 14 days, and the final observation was made on the 14th day after preparing the samples.

Disease severity was determined by comparing the actual count of the surviving plants in Pythium-inoculated soil with the actual count of the surviving plants in sterile soil.

Control effectiveness of the test compound was determined by comparing the actual count of surviving plants in the chemically treated soil with the actual count of surviving plants in the Pythium-inoculated soil.

Each test consists of at least three replicates.

The control effectiveness is expressed as percent control calculated by the following formula:

$$\% \text{ control} = 100\% \frac{(\text{number of surviving plants in treated soil})}{(\text{number of surviving plants in untreated soil})}$$

The amount of test chemical applied is expressed as pounds per acre (lb/A) for 6 inch depth of soil.

The number of oospores, mixed in the soil was 1,000 oospores per gram of dry soil.

TEST PROCEDURE FOR *Rhizoctonia solani*

A blend of sterile soil and mycelium of *Rhizoctonia solani* inoculum 5-7 days old, is made and a blend of sterile soil and the test compound (normally added to the soil as a solution) was made. Then the chemically treated soil was added to an equivalent weight of the Rhizoctonia-inoculated soil, and the mixture was placed in a blender and thoroughly blended. This blend was then equally divided, and each division was placed in a container, seeded with sugar beet seeds, and water sealed. The containers were then placed in a greenhouse operating at a temperature range of 70°-80° Fahrenheit and humidity range of 50-95 percent for 14 days.

Containers of sterile soil only, sterile soil plus chemical, sterile soil plus *Rhizoctonia inoculum* were also implanted with sugar beet seeds, and placed in the greenhouse.

The final observation was made after 14 days.

Control effectiveness of the test compound was determined by comparing the actual count of surviving plants in the chemically treated Rhizoctonia-inoculated soil with the actual count of plants surviving in the Rhizoctonia-inoculated soil.

Disease severity was determined by comparing the actual count of surviving plants in the Rhizoctonia-inoculated soil with the actual counts of surviving plants in sterile soil.

Percent Control was calculated as follows:

$$\% \text{ control} = 100\% \frac{(\text{number of surviving plants in chemically treated soil})}{(\text{number of surviving plants in chemically untreated soil})}$$

In these tests the amount of inoculum of *Rhizoctonia solani* per dry weight of soil used was 1.5 grams of mycelium per 3,000 milliliters of dry soil. Each test consisted of at least three replicates. The amount of chemical used to treat the soil is expressed as pounds per acre (lbs/A) based on a 6 inch depth of soil.

TEST PROCEDURE FOR *Fusarium solani*

A blend of sterile soil and spores of *Fusarium solani* and a blend of sterile soil and test compound (generally applied in the form of a solution) were made. A mixture of the Fusarium-inoculated soil and chemically treated sterile soil is thoroughly mixed in a soil blender. After blending, the mixture was equally divided and each division was placed into containers, seeded with California white pea beans, water sealed and placed in a greenhouse operating at a temperature range of 70°-80° Fahrenheit and a humidity range of 50-95 percent, for 21 days.

Containers of sterile soil only, sterile soil plus test compound, sterile soil plus *Fusarium inoculum* were also implanted with seeds of California white pea bean, watered and placed in the greenhouse.

Control effectiveness of the test compound was determined by comparing the actual infested stem area of the plants in the chemically treated Fusarium-inoculated soil with the actual infected stem area of the plants in the Fusarium-inoculated soil.

The percent control was calculated from the data based on the following formula:

$$\% \text{ control} = 100\% - \frac{[\text{infected stem area of plants in treated soil}]}{[\text{infected stem area of control plants}]} \cdot 100\%$$

Disease severity was determined by comparing the actual count of surviving plants from Fusarium-inoculated soil with the actual count of surviving plants from the sterile soil.

In these tests the amount of spores of *Fusarium solani* per dry weight of soil was $5 \times 10^6$ spores per 3,000 milliliters of soil. The final observation was made 21 days after putting the samples in the greenhouse.

Each test consisted of at least three replicates.

In all the above described tests the effect of the test compound upon the plants used in the test was also observed. The observations are expressed on the same scale as mentioned herein for the Herbicidal Tests.

The test results for the compounds as controls against the deleterious effects of soil fungi diseases are given in Table 3. In this Table, column 1 gives the example number, column 2 gives the test compound (unless otherwise indicated these were synthesized as described herein), columns, 3, 4, 5, and 6 gives the percent control against the diseases caused by *Sclerotium rolfsii* (Sr), *Pythium ultimum* (Pu), *Rhizoctonia solani* (Rs), and *Fusarium solani* (Fs), when the compounds are applied at 50 pounds per acre (lbs/A) per 6 inch depth of soil. For some compounds the results of repeated tests, or for lower application rates are shown. "0" percent means no control of the deleterious effect of the plant pest, and values greater than zero show control of the deleterious effect of the plant pest, "100" percent shows complete control of the deleterious effect of the plant pest; that is the plant pest had no effect under the conditions of the test.

TABLE 3

TEST RESULTS FOR CONTROL AGAINST THE SOIL FUNGI:

SR - *Sclerotium rolfsii*, Pu - *Pythium ultimun*, Rs -*Rhizoctonia solani*, and Fs -*Fusarium solani*

| Example No. | Compound | Percent Control at 50 Pounds Per Acre per 6 inch Depth of Soil | | | |
|---|---|---|---|---|---|
| | | Sr | Pu | Rs | Fs |
| XXVII | S-β-naphthyl N-methyl-thiolcarbamate | 0 | 0 | 0 | 0 |
| XXVIII | S-α-naphthyl N-methyl-thiolcarbamate | 79, 0[b], 0[c], 0[d] | 0 | 0 | 0[a] |
| XXIX | S-β-naphthyl N,N-dimethyl-thiolcarbamate[g] | 0 | 0 | 0 | 0[a] |
| XXX | S-α-naphthyl N,N-dimethyl-thiolcarbamate | 0 | 0[a] | 0 | 0[e] |
| XXXI | S-phenyl N-methyl-thiolcarbamate[e] | 39, 75, 52[b], 38[c] | 0 | 68, 42[b], 54[c], 48[d], N-ethyl48[b], 51[c] | 40[b], 10[c], 0[d] |
| XXXII | S-phenyl N-methyl-thiolcarbamate[e] | 43, 0[b], 0[c] 43, 46[b] | 0 | 46, 34[b], 40[c] | 35, 25[b], 27[c] |
| XXXIII | S-phenyl N-n-butyl-thiolcarbamate[e] | 32, 0[b], 0[c] | 0 | 23, 29[b], 31[c] | 13, 18[b], 0[c] |
| XXXIV | S-phenyl N,N-dimethyl-thiolcarbamate[e] | 0 | 0 | 68[a] | 67[f] |

[a]herbicidal effect on the plant, rating 4, 5, or 6
[b]control effectiveness at 25 pounds per acre
[c]control effectiveness at 12 pounds per acre
[d]control effectiveness at 6 pounds per acre
[e]known compound described in patents 2,977,209 and 3,265,563 and disclosed as a systemic nematocide in Applicant's copending application, SYSTEMIC NEMATOCIDES, Serial No. 408,775, filed October 23, 1973.
[f]herbicidal effect on the plant, rating 7, 8, or 9
[g]known compound described in Journal of Organic Chemistry, 31, pages 3980–3983

FOLIAR FUNGICIDAL PROTECTANT TESTS

EXAMPLES XXXV to XLII

These tests indicate if the test compound when applied to the foliage of a plant prior to the plant contacting a disease causing fungi, virus, or bacteria, protects the plant against the disease or deleterious effect of the plant pest. Tests were made against the following disease.

LRW — Leaf Rust of Wheat — caused by the fungus — *Puccinia rubigo-vera*

LBT — Late Blight of Tomatoes — caused by the fungus — *Phytophthorans infestans*

PMC — Powdery Mildew of Cucumbers — caused by the fungus — *Erysiphe cichoraceum* or *Pseudoperonospora cubensis*

TMV — Tobacco Mosaic Virus — caused by the virus — *Marmor tabacci*

BLT — Bacterial Leaf Spot of Tomatoes — caused by the bacterium — *Xanthomonas vesicatoria*

FWT — Fusarium Wilt of Tomatoes — caused by the fungus — *Fusarium oxysporum f. lycopersici*

RBD — Rice Blast Disease — caused by the fungus — *Piricularia oryzoe*

LEAF RUST OF WHEAT — TEST PROCEDURE

Pots of Cheyenne wheat plants, *Triticum vulgare*, which are approximately 7 to 8 days old, and 4 to 5 inches tall, were mounted on a turntable and sprayed for 60 seconds with a solution containing a pre-determined amount of compound, e.g., 1,000 parts per million (ppm) of S-β-naphthyl N-methylthiolcarbamate at 40 pounds per square inch (psi).

These treated plants were dried (4–8 hours), and then were inoculated with the disease by dusting the plants with spores of *Puccinia rubigo-vera* taken from diseased plants, and incubated at 70° F. at 90 percent relative humidity.

After incubating for 18 hours to insure that the plants are infested, the spore-inoculated plants are placed in a greenhouse maintained at a temperature range of 70°–80° Fahrenheit, and a humidity range of 50–90 percent. Observations of pustules were made 7 days after the plants were inoculated.

Control samples are also prepared by inoculation of plants with the spores of *Puccinia rubigo-vera*, incubated, and placed in a greenhouse for observation.

Control effectiveness against the disease (the deleterious effect of the plant pest) is determined by comparing the active counts of developed pustules on the chemically treated plants with the actual counts of developed pustules on the control plants.

Control effectiveness is expressed as Percent Control which is calculated as follows:

$$\text{Percent Control} = \left[100 - \frac{\text{Average number of Pustules on Treated Plants}}{\text{Average number of Pustules on Untreated Plants}}\right] \times 100\%$$

The average value of the percent control based on three replicates is the test value used. A "0" means no control of the deleterious effect of the plant pest, and "100" means complete control.

POWDERY MILDEW OF CUCUMBERS — TEST PROCEDURE

The test procedure for Leaf Rust of Wheat is followed using cucumber plants with 2 leaves of the 1st true leaf stage. Straight-8-cucumber plants - *Cumcumes sativas* were used. These plants are transferred to a mildew infection chamber having infected plants, and incubated for 18 hours at 80° F. and 95 percent humidity. The plants were then placed in a greenhouse for 10 days and the final observation of infected plants is made on the 10th day.

Control effectiveness was determined by comparison of the infected area of the chemically treated plant with those of the control sample.

The percent control was calculated as follows:

$$\% \text{ control} = 100\% - 100\% \frac{\text{(Average infected area of treated plants)}}{\text{(Average infected area of control plants)}}$$

TOBACCO MOSAIC VIRUS — TEST PROCEDURE

The test procedure for Leaf Rust of Wheat was followed, using tobacco plants *Nicotiana glutinosa*, which are grown from seeds until they have their first true leaves. After spraying the plants with the test compound and drying, the plants were inoculated by spraying the plant leaves with a solution containing an extract from tobacco mosaic-infested leaves and carborundum, and then rubbing the leaves to ensure epidermal cell rupture. The plants were then placed in the greenhouse for observation.

After about 10 days, the total infected area of the chemically treated plants were compared with those of the control samples.

The percent control is calculated as described for Leaf Rust of Wheat, by using the average area of the leaves affected by the virus.

LATE BLIGHT OF TOMATOES, *Phytophthorans infestans* — TEST PROCEDURE

The test procedure is similar to that for Leaf Rust of Wheat. Tomato plant species, Bonny Best Tomato having 5 true leaves, approximately 5 to 6 weeks old were chemically treated, dried, and inoculated in a suspension containing zoaspores and sporangia of *Phytophthorans infestans* by spraying the tomatoes with the suspension. The plants are incubated for 41 hours at 70° F. and 95 percent relative humidity, and observed for lesions visible to the naked eye. Control effectiveness is made by direct comparison of the number of lesions for the untreated plants with those of the chemically treated plants.

The percent control is calculated as follows:

$$\% \text{ control} = 100\% - 100\% \frac{\text{(number of lesions per treated plant)}}{\text{(number of lesions per control plant)}}$$

Inoculation consists of spraying at the rate of 100 milliliters of a suspension containing $10^6$ zoaspores and $10^5$ sporangia per 35 tomato plants.

BACTERIAL LEAF SPOT OF TOMATOES — TEST PROCEDURE

The test procedure for Leaf Rust of Wheat was followed. Tomato plants of the species Bonny Best with 3–5 leaves after 5–6 weeks growth were chemically treated, dried, and inoculated by spraying with a 200 milliliter solution containing three pharmaceutical bottles of 60 days old bacteria of *Xanthomanas vesicatoria* and 5 grams of carborundum. Each pharmaceutical bottle contained from 30,000 to 40,000 spores. The spraying rate was 200 milliliter of solution per 70 plants. The plants were incubated for 40 hours at 80° F. and 95 percent humidity and then placed in a greenhouse for 9 days and observed for lesions.

Control plants were also inoculated, incubated, and placed in a greenhouse.

Control effectiveness was determined by comparing the actual counts of lesions on the treated plants with those of the control plants.

The average percent control was calculated as follows:

$$\% \text{ control} = 100\% - 100\% \frac{\text{(average number of lesions in treated plants)}}{\text{(average number of lesions in control plants)}}$$

FUSARIUM WILT OF TOMATOES — TEST PROCEDURE

Tomato plants of the species Bonny Best were grown in sterile soil for 4–6 weeks until they had an average height of 6–8 inches and 3 to 4 true leaves, and were chemically treated by spraying and dried.

A blend of soil containing 10,000 to 20,000 spores of *Fusarium oxysporum f. lycopersici* per gram of dry soil was prepared, and the chemically treated plants were planted in this inoculated soil and placed in the greenhouse for 30 to 40 days.

Control effectiveness was determined by comparing the count of the number of chemically treated plants surviving with the count of the number of control plants surviving.

Percent control was calculated as described under the test procedure for Leaf Rust of Wheat by using the counts of the number of surviving plants.

RICE BLAST DISEASE — TEST PROCEDURE — PROTECTANT

Rice plants of the Nato variety were grown for 18 days until fully developed second stage leaf was attained.

These were chemically treated as described for the test procedure for Leaf Rust of Wheat and then inoculated with spores of the fungus *Piricularia oryzoe* by spraying with a solution containing $10^5$ spores per milliliter, at a rate of 200 milliliters per 70 plants.

The plants were incubated for 40 hours, at 80° F. and 95 percent humidity, then placed in the greenhouse for 5 days and observed for dark black to greyish spots.

Control plants are also inoculated with the fungus spores, incubated, and placed in the greenhouse.

Control effectiveness is determined by comparing the counts of the number of spots on the treated plants with those on the untreated plants. Three replicates are used.

Percent Control is calculated as follows:

% control =
$$100\% - 100\% \frac{\text{(Average number of spots on treated plants)}}{\text{(Average number of spots on control plants)}}$$

The foliar fungicidal test results are given in Table 4. Column 1 of Table 4 gives the example number; column 2 lists the test compound, which is prepared according to the synthesis given herein unless indicated otherwise; column 3 gives the percent control obtained at 1,000 parts per million (ppm) of the test compound for the diseases shown in the Table.

In all tests, the effect of the test compound on the plants was noted, and any effect was rated as described herein in the Herbicidal Test section.

For some compounds, the values of reported tests were given, as well as, values at lower test concentrations.

"0" percent means no control of deleterious effect of the plant pest; values greater than zero means control of the deleterious effect of the plant pest and "100" percent means complete control of the deleterious effect of the plant pest.

TABLE 4

Foliar Fungicidal Protectant percent control against the diseases: Leaf Rust of Wheat (LRW), Late Blight of Tomatoes (LBT), Powdery Mildew of Cucumbers (PMC), Tobacco Mosaic Virus (TMV), Fusarium Wilt of Tomatoes (FWT), and Rice Blast Disease (RBD). Test Concentration 1,000 parts per million (ppm). Note: Zero ("0") percent means no control and one hundred ("100") percent means complete control.

FOLIAR FUNGICIDAL TEST RESULTS

| Example No. | Compound Applied | Percent Control at Diseases ||||||
| | | LRW | LBT | PMC | TMV | FWT | RBD |
| --- | --- | --- | --- | --- | --- | --- | --- |
| XXXV | S-$\beta$-naphthyl N-methyl-thiolcarbamate | 0 | 0 | 0 | 0 | 25 | 0 |
| XXXVI | S-$\alpha$-naphthyl N-methyl-thiolcarbamate | 0 | 90 | 0 | 0 | 0 | 0 |
| | | NT | $84^a$ | NT | NT | NT | NT |
| | | NT | $24^b$ | NT | NT | NT | NT |
| | | NT | $0^c$ | NT | NT | NT | NT |
| XXXVII | S-$\alpha$-naphthyl N,N-dimethyl-thiolcarbamate | 87 | 76 | 0 | 0 | 0 | 96 |
| | | $94^a$ | NT | NT | NT | NT | $68^a$ |
| | | $89^b$ | NT | NT | NT | NT | $35^b$ |
| | | $59^c$ | NT | NT | NT | NT | $0^c$ |
| XXXVIII | S-$\beta$-naphthyl N,N-dimethyl-thiolcarbamate$^i$ | 0 | 51 | 0 | 0 | 0 | 0 |
| XXXIX | S-phenyl N-methyl-thiolcarbamate$^h$ | $100^e$ | 0 | 0 | 0 | 0 | 0 |
| | | $59^{a,d}$ | NT | NT | NT | $50^{a,g}$ | NT |
| | | $0^{b,d}$ | NT | NT | NT | $42^b$ | NT |
| | | $0^c$ | NT | NT | NT | $25^c$ | NT |
| | | $0^a$ | NT | NT | NT | NT | NT |
| XL | S-phenyl N-ethyl-thiolcarbamate | $0^b$ | $0^a$ | $0^a$ | $0^a$ | $42^a$ | $0^a$ |
| | | $0^c$ | $0^b$ | $0^b$ | $0^b$ | $50^b$ | $0^b$ |
| | | $42^c$ | $0^c$ | $0^c$ | $0^c$ | $42^c$ | $0^c$ |
| XLI | S-phenyl N-n-butyl-thiolcarbamate$^h$ | 0 | 0 | 0 | 0 | 0 | 0 |
| XLII | S-phenyl N,N-dimethyl-thiolcarbamate$^h$ | 0 | 0 | 0 | 0 | 0 | 0 |

$^a$test results at test concentration of 500 ppm
$^b$test results at test concentration of 250 ppm
$^c$test results at test concentration of 100 ppm
$^d$herbicidal effect on the plant, rating 1, 2, or 3
$^e$herbicidal effect on the plant, rating 4, 5, or 6
$^g$herbicidal effect on the plant, rating 10
$^h$described in U.S. Pat. No. 2,977,209 and U.S. Pat. No. 3,265,563, and disclosed as a systemic nematocide in Applicant's copending application entitled SYSTEMIC NEMATOCIDES, Ser. No. 408,775, filed October 23, 1973.
$^i$described in Journal of Organic Chemistry, 31, pages 3980–3983.

INSECTICIDAL TESTS

EXAMPLES XLIII to XLVII

These tests show the biological activity of the novel compounds disclosed herein against insects. Specific tests include: stomach poison tests, that is the compounds when ingested by the insect affect the insect; contact tests, that is the insects are covered or contacted with a solution of the compound which is absorbed by the insects; ovicidal tests, that is the compound's effect on eggs and larvae of the insect are determined. Procedures for these tests are as follows.

MITICIDAL CONTACT AND OVICIDAL TEST PROCEDURE

Potted horticultural bean plants (*Phaseolus vulgaris* L.) at a growth stage when the primary leaves are approximately one (1) inch long were infested, about 24 hours before being chemically treated, with about 20–25 adult female two-spotted mites (*Tetranychus urticoe*), and placed in a greehouse to insure establishment of mite colonies, eggs, and nymphs.

A stock acetone emulsion is prepared having the following composition by weight: 99.75 percent acetone, 0.20 percent sorbitan trioleate (Span 85), and 0.05 percent sorbitan monooleate polyoxyalkylene derivative (Tween 80). Test compound is dissolved in a portion of the stock acetone emulsion. Deionized water is added to yield a concentrated test solution containing about 10 percent acetone, 0.020 percent Span 85, and 0.0050 percent Tween 80. The amount of test compound dissolved in the stock acetone emulsion is such that when diluted with deionized water the concentrated test solution has the highest concentration (usually 1,000 ppm) of test compound used in the tests. Solutions which are prepared by diluting the concentrated test solution with a mixture of deionized water and stock acetone emulsion, which mixture contains about 10 percent acetone, 0.020 percent Span 85, and 0.0050 percent Tween 80. Thus, all test solutions always contain about 10 percent acetone, 0.020 percent Span 85, and 0.0050 percent Tween 80, irrespective of the concentration of test compound.

In some cases where the compound was difficult to dissolve it was coated on a previously tested inert base material containing wetting agents so as to form a 50 weight percent wettable powder which was then diluted to form a suspension having the desired concentration of test compound.

The infested host plants were removed from the greenhouse, and dipped into the slightly agitated solution or suspension of the test compound, and were air dried, placed in the greenhouse and watered by a subterranean source and observed.

After 72 hours in the greenhouse, one leaf is removed and the effect on the mites mortality or other physiological effects are noted (Contact Test). Seven days later, the second leaf was removed and final physiological observations were made on the newly emerged nymphs, and eggs (Ovicidal Test). These observations are expressed as percent mortality, for the initial effect on mites (contact) and, for the effect on eggs and nymphs (ovicidal).

The values of percent control reported are based on at least three replicates, and are calculated as follows:

$$\text{(Contact) Percent Control} = \frac{\text{(number of dead mites)}}{\text{(total number of mites)}} \times 100\%$$

(Ovicidal) Percent Control =
$$\frac{\text{(number of dead eggs and nymphs)}}{\text{(total number of eggs and nymphs)}} \times 100\%$$

INSECTICIDE-STOMACH POISON — MEXICAN BEAN BEETLE — TEST PROCEDURE

Potted horticultural bean plants (*Phaseolus vulgaris* L.) at a growth stage where the primary leaves are 2.5 inches long, were dipped into a slightly agitated solution or suspension of the test compound (prepared as described previously), air-dried, placed in a greenhouse, and watered by a subterranean source. After drying, the plants were infested with third (3rd) instar larvae of the Mexican Bean Beetle (*Epilachona varivestis*).

For some tests the larvae were placed on the plants by enclosing the plant within a spherical wire mesh cage containg the larvae. In other tests the treated plant leaves are detached from the plant and placed on moistened filter paper in a petri dish in the laboratory and the larvae are brushed on to the plant leaves, then the dish is covered. Five larvae are used per replicate of the test, and at least three replicates are used.

After 72 hours the larvae are observed for mortality or other significant physiological effects, such as distorted growth.

The effectiveness of the compound at the test concentration is expressed as percent control calculated as follows:

$$\% \text{ control} = \frac{\text{(number of dead larvae)}}{\text{(total number of larvae)}} \times 100\%$$

SOUTHERN ARMY WORM-STOMACH POISON — TEST PROCEDURE

This procedure is similar to that described above for the Mexican Bean Beetle-Stomach Poison - test procedure. In this case, 7 day old larvae (4th instar) of the southern worm (*Spodopter eridania*), which are about ⅜ inch long are brushed on the plant leaves. Five larvae per test replicate were used, and a minimum of 3 replicates were made. Observations are made after 72 hours for mortality or other effects on the larvae.

The efficiency of the test compound at the concentration used is expressed as percent control calculated as follows:

$$\% \text{ control} = \frac{\text{(number of dead larvae)}}{\text{(total number of larvae)}} \times 100\%$$

PEA APHID-CONTACT — TEST PROCEDURE

Enclosed wire mesh cages, each cage containing 10 adult pea aphids (*Acyrthosiphon pisum*), were mounted on a turntable, and sprayed with the test solution or suspension for 5 seconds at 20 pounds per square inches, so that the aphids were completely covered by the test solution. The cages are then placed over potted broad bean plants (*Vicia sabae*) for infestation by the chemically treated aphids. The enclosed potted plants were placed in the greenhouse and watered by a subterranean source.

After 3 days, the aphids are observed for mortality and other physiological changes, such as sterility, abnormal egg production, or nymphs.

The effectiveness of the test compound is expressed as percent control calculated as follows:

$$\% \text{ control} = \frac{\text{(number of dead aphids, nymphs, larvae)}}{\text{(total number of aphids, nymphs, larvae)}} \times 100\%$$

HOUSEFLY-CONTACT — TEST PROCEDURE

About 25 to 30, 3 day old adult houseflies (*Musca domestica*) were transferred to a spherical mesh cage which was mounted on a turntable in a hood, and sprayed while rotating with 1 milliliter of the test solution, which is a suspension or solution of the test compound in a 3:1 mixture of kerosene/cyclohexanone. Food and moisture was then supplied to the cage, and observations were made 15 minutes after spraying and again at 72 hours after spraying to determine the effect of the compound on the flies. Three test replicates were made.

The effectiveness of the test compound is expressed as percent control calculated as follows:

$$\% \text{ control} = \frac{\text{(number of dead flies)}}{\text{(total number of flies)}} \times 100\%$$

MOSQUITO LARVAE CONTROL — TEST PROCEDURE

A small plastic cup was filled with 100 milliliters of the test solution, some dried dog food, and infested with 5 yellow fever mosquito larvae, young of the 4th instar stage (*Aedes aegypti*), and capped and held at 70°-80° F.

The test results for the insecticidal tests are given in Table 5. The first column of Table 5 gives the example number; the second column lists the test compound (unless otherwise indicated, the compound was synthesized as disclosed herein); column 3 gives the percent control at the test concentration shown in Table 5.

Note: "zero" percent (0%) control indicates no effect on the plant pests; intermediate values indicates an effect upon the plant pests; and "one hundred" percent (100%) control indicates all plant pests killed or affected.

TABLE 5

Standard test concentration - 1,000 parts per million (ppm) for MBB, SAW, TSM - C, TSM - O, HF - C, and PA - C, tests; 50 parts per million (ppm) for TSM - S, tests; and 10 parts per million (ppm) for MOL tests.

INSECTICIDAL TEST RESULTS

| Example No. | Compound Applied | Percent Control | | | | | | | |
|---|---|---|---|---|---|---|---|---|---|
| | | MBB | SAW | TSM - C | TSM - O | HF - C | PA - C | TSM - S | MOL |
| XLIII | S-α-naphthyl N,N-dimethyl-thiolcarbamate | 0 | 0 | 50[a] | 0 | 0 | 0 | 0 | 0 |
| XLIV | S-α-naphthyl N-methyl-thiolcarbamate | 0[b] | 0 | 0 | 0 | 0 | 0 | 0 | |
| XLV | S-β-naphthyl N,N-dimethyl-thiolcarbamate[e] | 0 | 0 | 0 | 0 | 0 | 0 | 0 | |
| XLVI | S-phenyl N-methyl-thiolcarbamate[c] | 33 | 0 | 0 | 0 | 0 | 13 | 0 | |
| XLVII | S-phenyl N,N-dimethyl-thiolcarbamate[d] | 0 | 0 | 0 | 0 | 0 | 10 | 0 | |

[a] herbicidal effect, rating 1, 2, or 3
[b] herbicidal effect, rating 4, 5, or 6
[c] described in U.S. Pat. No. 2,977,209 and U.S. Pat. No. 3,265,563 and disclosed as a systemic nematocide in Applicant's copending application, SYSTEMIC NEMATOCIDES, Ser. No. 408,775, filed October 23, 1973.
[d] described in U.S. Pat. No. 2,977,209
[e] described in Journal of Organic Chemistry, 31, pages 3980-3983.
MBB - Stomach Poison - for Mexican Bean Beetle
SAW - Stomach Poison - for Southern Army Worm
TSM - C - Contact Poison - for Two Spotted Spider Mite
TSM - O - Ovicidal Poison - for Two Spotted Spider Mite
HF - C - Contact Poison - for House Fly
TSM - S - Systemic Poison - For Two Spotted Spider Mite
PA - C - Contact Poison - for Pea Aphid for observation.

After 24 hours the cups are observed for physiological effect of the test compound on the larvae.

The effectiveness of the test compound is expressed as percent control calculated as follows:

$$\% \text{ control} = \frac{\text{(number of dead larvae)}}{\text{(total number of larvae)}} \times 100\%$$

SYSTEMIC CONTROL — OF TWO-SPOTTED SPIDER MITE TEST PROCEDURE

A potted horticultural bean plant (*Phaseolus vulgaris* L.), having two primary growth leaves, was transplanted to a pot containing 50 grams of a loam soil mixture (2:1 loam/sand). 20 milliliters of a test solution was placed at the center of the root ball, and the potted plant was water sealed, and placed in a greenhouse for 3 hours to allow the test compound to be taken up by the plants.

The potted plants were removed from the greenhouse and infested with 20 to 25 adult larvae, two-spotted spider mites (*Tetranychus urtical*) as previously described herein, and then returned to the greenhouse for holding.

Observations are made at the end of 72 hours and at the end of 7 days, and the efficacy of the test compound is reported as percent control previously described herein.

In all tests the effect of the test compounds on the plants were observed and reported in terms of the Herbicidal Scale described herein.

HERBICIDAL TESTS

EXAMPLES XLVIII TO LIII

These tests examples illustrate the preemergence and postemergence herbicidal activity of the compounds mentioned herein against undesirable plants (weeds).

The following test procedures were used.

The weed and crop species were seeded in individual 3 inch plastic pots filled with sandy loam type soil to a depth of about 1.75 inches. The number of seeds seeded depended upon their size, germination rate, and size of the plant. Generally sufficient seed was introduced to yield from 10 to 20 plants per pot, under normal growth conditions. The seeds were then covered with from 0.2 to 0.25 inches of sand.

For preemergence tests, the pots were sprayed with the test compound at planting of the seeds.

For postemergence tests, the pots after seeding according to a germination schedule were transferred to the greenhouse for germination and growth of the plants to their first true leaf stage before applying the test compound to the plant and soil.

Unless otherwise indicated, the test compounds were applied in the form of a spray, at a spray rate of 50 gallons per surface acre of soil. The pots of seeds (preemergence tests) or pots of plants (postemergence tests) were loaded into separate carrying trays (each tray carrying only pots for preemergence testing, or only pots for postemergence testing) and the trays were loaded unto a conveyor belt which travels at about 1.5 miles per hour through a spraying unit equipped with a Tee Jet 8003-E nozzle tip. As the tray passes into and out of the spraying unit, it trips solenoid valves which activates and deactivates the sprayer. The sprayer operated in the range of 45–50 pounds per square inch of pressure, with compressed air.

Immediately after the spray treatment, the pots with the postemergence test plants were transferred to the greenhouse, but the pots containing preemergence test plants were watered with a gentle surface spray of water to more evenly distribute the test compound throughout the pot and were then transferred to the greenhouse. The treated test plants were grown under greenhouse conditions using natural sunlight at a temperature of 75° ± 10° F. and a humidity of 75 ± 20 percent. The treated pots were observed daily for interim response. The final observations unless otherwise indicated for postemergence treated plants were made approximately 13 days after treatment. Final observation for preemergence treatment unless indicated otherwise were made 20 days after treatment.

Observations included all abnormal physiological response of stem bending, petiole curvature, epinasty, hyponasty, retardation, stimulation, root development, necrosis, and related growth regulant characteristics.

Observations were reported on injury ratings, based on a scale of zero (0) which indicates no injury, to ten (10) which indicates complete kill; that is all plants in all replicates are dead. The intermediate numbers include the following: one (1) trace injury; two, three (2, or 3) a slight injury, from which the plants recover, with no reduction in growth; four, five, or six (4, 5, or 6) moderate injury, plants recover but with reduced growth; and seven, eight, or nine (7, 8, or 9) severe, plants do not recover from the injury.

For these tests, the test compounds were dissolved in the standard solvent mixture of acetone, methanol, dimethylformamide, 90:8:2 volume per volume (v/v), and an aliquot part removed and diluted with distilled water for the pre-selected application rate.

The weed species used for preemergence tests were:

YNSG — yellow nutsedge — *Cyperus esculentus* L.
WOAT — wild oats — *Avena fatua*
JMWD — jimosonweed — *Datura stramonium* L.
VTLF — velvetleaf — *Abutilon theophrasti* Medic
JNGS (S) — johnsongrass — *Sorghum halepense* (L.) Pers. (grown from seeds)
LMQR — lambsquarter (common) — *Chenopodium album* L.
MSTD — wild mustard — *Brassica kaber* (D.C.) L. C. Wheeler var. pinnatifida (Strokes) L. C. Wheeler
YLFX — yellol foxtail — *Setaria glauca* (L.) Beauv.
BNGS — barnyardgrass — *Echinochloa crusgalli* (L.) Beauv.
CBGS — large crabgrass — *Digitaria sanguinalis* (L.) Scop.
BKWT — wild buckwheat — *Polygonum convolvulus* L.
MNGY — mixture of tall morningglory and ivyleaf morningglory — mixture of *Ipomoea purpurea* (L.) Roth and *Ipomoea hederacea* (L.) Jacq.

The weed species used for postemergence tests were:

YNGS — yellow nutsedge — *Cyperus esculentus* L.
WOAT — wild oats — *Avena fatua*
JMWD — jimsonweed — *Datura stramonium* L.
VTLF — velvetleaf — *Abutilon theophrasti* Medic
JNGS (S) — johnsongrass — *Sorghum halepense* (L.) Pers. (grown from seeds)
MSTD — wild mustard — *Brassica Kaber* (D.C.) L. C. Wheeler var. pinnatifida (Stokes) L. C. Wheeler
YLFX — yellow foxtail — *Setaria glauca* (L.) Beauv.
BNGS — barnyardgrass — *Echinochloa crusgalli* (L.) Beauv.
BKWT — wild buckwheat — *Polygonum convolvulus* L.
MNGY — mixture of tall morningglory and ivyleaf morningglory — mixture of *Ipomoea purpurea* (L.) Roth and *Ipomoea hederacea* (L.) Jacq.
CTHS — Canadian thistle grown from Rhizomes — *Cirsium arvense* (L.) Scop.
COTN — cotton — *Gossypium domestica*

The herbicidal test results are given in Table 6. Column 1 of Table 6 gives the example numbers; column 2 lists the test compound applied (unless otherwise indicated, the compound used was synthesized as disclosed herein); column 3 lists the preemergence test results as a herbicidal rating described herein. Only the weed species in which the herbicidal rating was greater than 5 are listed. The standard test application rate was 10 pounds per acre (10 lbs./A) unless otherwise indicated. In some cases the results of repeated tests are shown. Column 4 lists only the postemergence herbicidal rating of greater than 5, unless otherwise indicated. The standard test application rate was 10 pounds per acre (10 lbs./A) unless otherwise indicated.

TABLE 6

HERBICIDAL ACTIVITY AGAINST WEEDS
Preemergence Application Rate 10 lbs./A
and
Postemergent Application Rate 10 lbs./A

| Example No. | Compound Applied | Preemergence Rating Weed | Rating | Postemergence Rating Weed | Rating |
|---|---|---|---|---|---|
| XLVIII | S-α-naphthyl N-methyl-thiolcarbamate | a | | a | |
| XLIX | S-α-naphthyl N,N-dimethyl-thiolcarbamate | YLFX | 9 | JMWD | 9 |
| | | BNGS | 8 | MSTD | 10 |
| | | CBGS | 10 | BKWT | 10 |
| | | PIGW[b] | 7 | | |
| L | S-β-naphthyl N,N-dimethyl-thiolcarbamate | a | | MSTD | 10 |
| | | | | JMWD | 9 |
| LI | S-β-naphthyl N-methyl-thiolcarbamate | a | | a | |
| LII | S-phenyl N-methyl-thiolcarbamate[d] | a | | JMWD | 10 |
| | | | | VTLF | 6 |
| | | | | CTHS (R) | 9 |
| LIII | S-phenyl N,N-dimethyl-thiolcarbamate[e] | WOAT | 8 | JMWD | 9 |
| | | PIGW[b] | 7 | CTHS (R) | 10 |
| | | MSTD | 7 | COTN | 6 |
| | | YLFX | 8 | BKWT | 6 |

TABLE 6-continued
HERBICIDAL ACTIVITY AGAINST WEEDS
Preemergence Application Rate 10 lbs./A
and
Postemergent Application Rate 10 lbs./A

| | | Preemergence Rating | | Postemergence Rating | |
|---|---|---|---|---|---|
| Example No. | Compound Applied | Weed | Rating | Weed | Rating |
| | | BNGS | 7 | BNGS | 8 |
| | | CBGS | 9 | | |
| | | c | | | |

$^a$no significant effect on any species at 10 pounds per acre - rating zero "0" to four (4)
$^b$tested against PIGW - redroot pigweed - *Amaranthus retroflexus* L.
$^c$no effect on any species when tested at 5 pounds per acre, 2 pounds per acre, and 1 pound per acre - rating zero "0"
$^d$described in U.S. Pat. No. 2,977,209 and U.S. Pat. No. 3,265,563, and disclosed as a systemic nematocide in Applicant's copending application entitled, SYSTEMIC NEMATOCIDES, Ser. No. 408,775, filed October 23, 1973.
$^e$described in U.S. Pat. No. 2,977,209

APPLICATION

CONTROL OF NEMATODES a. Systemic Control

The deleterious effects of Meloidogyne species othan than *Meloidogyne icognita* may also be systemically controlled by use of the novel S-α-naphthyl and S-β-naphthyl thiolcarbamates of the general formulas disclosed herein, wherein $R_1$ is hydrogen. Preferably $R_2$ is a straight chain alkyl, particularly of from one to three carbon atoms. The species *Meloidogyne exigua* (Coffee Root-knot Nematode), *Meloidogyne arenaria* (Peanut Root-knot Nematode), *Meloidogyne hapla* (Northern Root-knot Nematode), and Citrus root Nematode are examples of other Meloidogyne species which may be controlled. *Ditylonchus destructor* (Potato Rot Nematode) may also be controlled by these compounds. The *Meloidogyne icognita* nematode in particular is systemically controlled by the compounds S-α-naphthyl N-methylthiolcarbamate and S-β-naphthyl N-methylthiolcarbamate and others of the general formulas described herein, in which $R_1$ is hydrogen and $R_2$ is a straight chain alkyl of from one to five carbon atoms.

b. Soil and Other Control of Nematodes

Other species of nematodes may be controlled by applications other than systemic foliage contact, for example, by applying S-β-naphthyl N-methylthiolcarbamate, or other S-β-naphthylthiolcarbamates of the general formula wherein $R_1$ is H, and $R_2$ is a straight chain alkyl of from one to five carbon atoms, preferably those alkyls with one to three carbon atoms, disclosed herein, to the soil, or by dipping the bulbs in solutions. Some examples of these other nematodes are:

| | |
|---|---|
| *Aphelenchoides* species | Bud and Leaf Nematodes |
| *Anguina tritici* | Wheat Nematode |
| *Anguina agrostis* | Grass Nematode |
| *Belonolaimus* species | Sting Nematodes |
| *Criconemoides* species | Ring Nematodes |
| *Ditylonchus dipsaci* | Stem and Bulb Nematode |
| *Ditylonchus angustus* | Rice Nematode |
| *Dolichodorus heterocephalus* | Awl Nematode |
| *Helicotylenchus* species | Spiral Nematodes |
| *Heterodera rostochiensis* | Golden Nematode |
| *Heterodera tabacum* | Tobacco Cyst Nematode |
| *Heterodera schachtii* | Sugar Beet Nematode |
| *Heterodera carotae* | Carrot Root Nematode |
| *Heterodera gottingiana* | Pea Root Nematode |
| *Heterodera glycines* | Soybean Cyst Nematode |
| *Hoplolaimus* species | Lance Nematodes |
| *Pratylenchus brachyurus* | Smooth-headed Lesion Nematode |
| *Pratylenchus* species | Meadow Nematodes |
| *Pratylenchus musicola* | Banana Nematode |
| *Pratylenchus Zeae* | Corn Nematode |
| *Radopholus similis* | Burrowing Nematode |
| *Rotylenchus reniformis* | Kidney-shaped Nematode |
| *Trichodorus* species | Stubby-root Nematodes |
| *Tylenchorhynchus claytoni* | Tobacco Stunt Nematode |
| *Xiphinema* species | Dagger Nematodes | c. Application of the Compounds With Other Known Agricultural Compositions

S-α-naphthyl N-methylthiolcarbamate and S-β-naphthyl N-methylthiolcarbamates themselves and the other compounds disclosed herein having activity against nematodes may also be applied directly to the area where the deleterious effects of the nematodes are to be controlled, particularly against Meloidogyne species, especially *Meloidogyne incognita* species. It is, however, preferably to use suitable agricultural formulations which contain other ingredients which enhance application of this compound. These agricultural formulations will generally contain from 5 percent to 95 percent by weight of the novel thiolcarbamates of the other compounds disclosed herein, or mixtures of these compounds, and either from 1 percent to 95 percent by weight of an agricultural diluent, or from 1 percent to 20 percent by weight of a surface active agent and other ingredients required to produce wettable powders, dusts, solutions, emulsifiable concentrates, granules, and the like, or both.

For the control of a wider range of crop-pests and diseases it may be desirable to combine the thiolcarbamates with from 0.05 to 4 parts by weight of insecticides and fungicides, etc., known to be effective against crop-pests and diseases in the form of a concentrated premix, or during the application step for foliar applications. Examples of such pesticides which may be used in such combination are: granules containing stable metal azide-metal salt formulations disclosed in assignee's copending application entitled AZIDE-METAL SALT FORMULATIONS, Ser. No. 624,357, filed Oct. 21, 1975, Sevin (1-naphthyl-N-methylcarbamate), Chlorobenzilate (ethyl 4,4'-dichlorobenzilate), Guthion (O,O-diethyl-S-[4-oxo-1,2,3-benzotriazin-3(4H)-ylmethyl]phosphorodithioate), Disyston (O,O-diethyl-S-[2-ethylthio)ethyl]phosphorodithioate), Maneb (manganous ethylene bisdithiocarbamate), Karathane (mixture of 2,4-dinitro-6-octylphenylcrotonate, 2,6-dinitro-4-octylphenylcrotonate, nitrooctylphenols (principally dinitro), 4-(1-methylheptyl)2,6-dinitrophenylcrotonate, 4-(1-ethylhexyl)2,6-dinitrophenylcrotonate, 4-(1-propylpentyl)2,6-dinitrophenylcrotonate, 6-(1-methylheptyl)-2,4-dinitrophenylcrotonate, 6-(1-ethylhexyl)2,4-dinitrophenylcrotonate, and 6-(1-propylpentyl)2,4-dinitrophenylcrotonate), Blasticidin (blasticidin-S-benzylaminobenzensulfonate), Benlate (methyl 1-(butylcarbamoyl)-2-benzimidazolecarbamate), or Plantvax (5,6-dihydro-2-methyl-1,4-oxathiin-3-carboxanilide-4,4-dioxide).

In some instances it is also desirable to include special purpose additives which will inhibit corrosion, reduce foaming, reduce caking, or increase flocculation.

S-β-naphthyl N-methylthiolcarbamate and the other naphthyl thiolcarbamates disclosed herein when used to control the deleterious effects of nematodes upon plants and plant parts, are applied in an effective amount as a suitable agricultural formulation within the vicinity of the infested area where the deleterious effects of the nematodes are to be controlled.

The phrase "to control the deleterious effects of nematodes upon plants and plant parts" as used herein, refers to reducing in intensity the adverse effects of the nematodes upon the plants. This may be by direct control or by systemic control which is obtained as a result of control mechanisms, such as (a) direct killing of the nematodes; (b) repelling of the nematodes; or (c) rapid healing of the plant attacked by the nematode. In systemic control, S-β-naphthyl N-methylthiolcarbamate and the other compounds exhibiting systemic nematode control are applied within the vicinity of the infested area, e.g., to the foliage of the plant which has its roots infested by root nematodes, rather than directly to the infested area, e.g., the plant roots themselves. Systemic control may result from a single mechanism of from a combination of mechanisms. It may result from a translocation of the compound, i.e., S-β-naphthyl N-methylthiolcarbamate (or a metabolite thereof) from its application site (e.g., the foliage), or to the area deleteriously affected by the nematodes (e.g., the roots, or the center portion of the stem) where it controls the deleterious effect; by (a) killing the nematodes; (b) repelling the nematodes; or (c) by healing the plant; or from translocation into the plant enzyme system where it induces the enzyme system to produce chemicals which (a) kill the nematodes or (b) repel them, or (c) which promote rapid healing of the plant. Systemic control may also result from a translocation of such a compound (or a metabolite of it) from its application site (foliage) through the plant to outside of the area (the roots) deleteriously affected by nematodes where it provides a protective shield against the nematodes; such as a root coating which repels or kills nematodes feeding upon this area of the plant.

d. The Effective Amounts Required to Control Nematodes

The effective amount varies with the particular nematode involved, the application method used, e.g., systemic, soil incorporation, or dusting with a powder, the type of formulation utilized, the plant species to be protected, the local conditions such as temperature, humidity, moisture content of the soil, nature of the soil and the like. Since many factors are involved, different rates of application are selected for best results depending upon these specific conditions.

The phrase "applied to the parts of the plant" as used herein refers to any method of application as by spraying or dusting the part of the plant which is aboveground, such as its foliage, bark or stem, or plant parts which are underground, such as bulbs, canes, tubers, or roots with these compounds.

For systemic control, S-β-naphthyl N-methylthiolcarbamate and the other disclosed compounds having systemic nematode control are applied preferably as a spray to the foliage of plants, particularly plants growing in soil infested with root-knot nematodes of the Meloidogyne species, particularly *Meloidogyne incognita*.

For other nematodes, it is possible to apply the compounds by dipping the canes, or tubers, or bulbs affected by nematodes which attack these parts of the plants into solutions containing one or more of the compounds or by dusting these parts with granules or powders containing such compounds.

For systemic control of Meloidogyne species, particularly *Meloidogyne incognita*, the effective amount of S-β-naphthyl N-methylthiolcarbamate and other novel compounds exhibiting systemic nematode control is a solution containing from 5 ppm to the maximum amount of the component tolerated by the plants applied as a spray to the dripping point. In general it is from 5 ppm to 4,000 ppm, normally from 5 ppm to 500 ppm, and preferably from 5 ppm to 200 ppm.

The same effective amounts of these compounds, i.e., S-β-naphthyl N-methylthiolcarbamate are applied when the compounds are used in combination with insecticides such as Sevin, Chlorobenzilate, Guthion, Disyston, or foliar fungicides such as Maneb, Karathane, Blasticidin, Benlate, or Plantvax. The amount of these other insecticides or fungicides will be in accordance with the label instructions disclosed in technical literature given with these known commercial compounds. In some cases, better control of the deleterious effects of nematodes is obtained when S-β-naphthyl N-methylthiolcarbamate or the other compounds are used in combination with the aforementioned insecticides and foliar fungicides.

Other application methods may include spraying above-ground parts such as stems, leaves and buds of plants in which nematodes are already present or where later attack is expected. Examples of these other applications are: dipping or soaking the reproductive parts in an aqueous suspension, solution or emulsion of an active ingredient; dusting above-ground parts or reproductive parts with a dust composition of an active ingredient; or immersing the root system to disinfect the plant or to provide protection against subsequent nematode invasion. The reproductive parts may be seeds, cane pieces, and bulbs which are infested or are to be planted in infested soil.

The effective amount of the novel compounds such as S-β-naphthyl N-methylthiolcarbamate for applying directly to the infested area in which nematodes are present, or directly to areas which may become infested with nematodes is from 40 to 100 pounds of a compound per acre, and preferably from 50 to 75 pounds per acre. Of course, higher rates may also be used.

e. Other Methods of Using the Compounds In Combination With Other Agricultural Compounds, Particularly Nematocides For a more effective control of the deleterious effects of root-knot nematodes upon plants, particularly Meloidogyne species, especially *Meloidogyne incognita*, it is preferable to apply a control nematocide such as a stable metal azide, stable metal azide-metal salt formulations of azides, Nemagon, or S-β-naphthyl N-methylthiolcarbamate to the soil before planting the crops so as to reduce the number of pathogenic nematodes contained therein, and then after planting the crop to maintain control of the deleterious effects of nematodes on the plants by applying an effective amount of S-β-naphthyl N-methylthiolcarbamate or S-α-naphthyl N-methylthiolcarbamate or other systemic nematode controlling compound to systemically control the deleterious effects of the nematodes.

It is best to remove as much of the pathogenic pests from the soil by applying azide compounds mentioned herein, or Nemagon, Nemacur, or the thiolcarbamates disclosed herein as well as Nemagon (1,2dibromo-3-chloropropane), Nemacur (ethyl 4-(methylthio)-m-tolybisopropylphosphoramidate) as well as soil fungicides and insecticides, such as: Captan (cis-N-((trichloromethyl)thio)-4-cyclohexene-1,2-dicarboximide), Dexon (p-dimethylaminobenzenediazo sodium sulfate), PCNB (pentachloronitrobenzene), Furadan (2,3-dihydro-2,2-dimethyl-7-benzofuranylmethylcarbamate), Mocap (O-ethyl S,S-dipropylphosphorodithioate), or Temik (2-methyl 2(methylthio)propionaldehyde O-(methylcarbamoyl)oxime), prior to planting the crops followed by one or more applications of S-α-naphthyl N-methylthiolcarbamate, or S-β-naphthyl N-methylthiolcarbamate, or mixtures thereof to the plant's foliage during plant growth to maintain better systemic control of the deleterious effects of nematodes.

The systemic nematode controlling compounds disclosed herein, especially S-α-naphthyl N-methylthiolcarbamate, or S-β-naphthyl N-methylthiolcarbamate are effective to control the deleterious effect of nematodes particularly Meloidogyne species and in particular *Meloidogyne incognita* upon plants affected by these nematodes; especially plants such as ornamentals, banana, avocado, sugar cane, pineapple, tobacco, citrus, soybeans, coffee, peanuts, corn, cucumbers, or garden crops such as sweet potato, tomato, carrot, celery, sugar beets, potato, etc.

The following example illustrates a suitable emulsifiable concentrate formulation for dilution in water for spraying plants, particularly, plant foliage or for application to other plant parts as herein mentioned.

EXAMPLE LIV

EMULSIFIABLE CONCENTRATE FORMULATIONS

| | Weight % |
|---|---|
| S-β-naphthyl N-methylthiolcarbamate | 13 |
| Xylene | 41 |
| Isophorone | 41 |
| Atlox(R) 3404* | 1 |
| Atlox(R) 3403 F* | 4 |

*Commercial emulsifiers for agricultural pesticides manufactured by Atlas Powder Co., Wilmington, Delaware, and registered with the U.S. Food and Drug Administration.

CONTROL OF OTHER PLANT PESTS a. Method of Application and Effective Amounts

The novel compounds described herein when used as fungicides, or insecticides, or herbicides are applied in an amount effective to control the plant pests such as weeds, insects, nematodes, fungi, bacteria, viruses, and other pathogenic organisms and microorganisms. These plant pests include those specifically described and shown herein as well as equivalent species which are biologically related and may be controlled by application of the compounds.

A single compound may be used in the formulation described herin, preferably a plurality of the compounds are used together either in a formulation or by concurrent application, that is, applying one or more compounds to the soil and one or more of the same or different compounds to the plant itself. In other applications, one or more compounds may be applied to the soil, or the plant, and within about 10 days, one or more of the same compounds, or different compounds may be applied to either the soil or the plant so as to effectively control plant pests.

When aplied as insecticides, the rate of application is from 20 parts per million to the amount tolerated by the plant, generally from 500 to 1000 parts per million of one or more of the active compounds, applied as a solution to the point of run off, or as a powder or dust which thinly coats the plant parts desired to be covered.

The same amounts are used when the compounds are applied as foliar fungicides.

As soil fungicides, the amount is from 0.5 pounds per acre to the maximum tolerated by desirable plants, generally from 1.0 pound per acre to 200 pounds per acre, per 6 inch depth of soil, preferably from 20 pounds per acre to 100 pounds per acre per 6 inch depth of soil.

As herbicides, the compounds are applied to the soil in any manner of application for preemergence control of weeds, generally at a rate from 2 pounds per acre to the maximum tolerated by the desirable plants, normally from 1 pound to 100 pounds per 6 inch acre, and preferably from 10 pounds to 50 pounds per 6 inch acre. For postemergence application, these same amounts may be used in the soil, or may be applied directly to the undesirable plants (weeds), using any manner of application which is sufficient to apply the compound or compounds in an effective amount.

The concentration of S-α-naphthyl N-methylthiolcarbamate or other appropriate thiolcarbamate disclosed herein in the emulsifiable concentrate may vary from 5 to 15 weight percent, the xylene may vary from 35 to 45 weight percent, isophorone may vary from 38 to 45 weight percent, Atlox ® 3404 may vary from 0.5 to 3.0 weight percent and Atlox ® 3403 F may vary from 3 to 6 weight percent.

As used in the claims and herein, the phrase "controlling plant pests" means decreasing the number of the plant pest itself, or its deleterious effect of plant pest, or both. The phrase "applying as to affect said plant pest" as used herein and in the claims means applying the compound in any of the ways illustrated herein, or presently known in the art of agriculture, so as to cause the deleterious effect of the plant pest to be decreased, or to cause the plant pest itself to be decreased, such as killed, wounded, or reproductively changed so as not to deleteriously affect the desirable plants, or to cause both the deleterious effect of the plant pest to be decreased and the plant pest itself to be decreased.

The phrase "an amount effective to control said plant pest" as used herein and in the claims means that amount required, as set forth herein, wherein the plant pest itself, or the deleterious effect of the plant pest, or both the plant pest itself and its deleterious effect on the desirable plants are decreased. The exact amount will vary depending upon the various factors such as resistance of plant to the pest, the inoculum density, temperature, time of planting, which factors are well described by Ralph Baker — "The Dynamics of Inoculum" page 395 — *Ecology of Soil Borne Plant Pathogens*, K. F. Baker and C. Snyder Ed.; University of California, Press, Berkeley, Calif., 1965, pages 395–419.

b. Specific Plant Pests the Compounds Are Effective Against

In summary, the novel compounds disclosed herein are effective against plant pests. When applied to plants, some are effective to systemically control nematodes, particularly the Meloidogyne species, and especially *Meloidogyne incognita*.

Those compounds of the general formula wherein the naphthyl in β-naphthyl, $R_1$ is hydrogen, and $R_2$ is an alkyl of up to five carbon atoms may also be applied directly to the soil as well as the plant itself to control these Meloidogyne nematodes, and their equivalent species. These compounds may also be applied to plants to control foliar fungus disease of Fusarium wilt of tomatoes and related diseases.

In addition to controlling nematodes systemically, those compounds of the general formula wherein naphthyl is α-naphthyl, $R_1$ is hydrogen, and $R_2$ is an alkyl of up to five carbon atoms, may be applied directly to the soil to control diseases caused by the fungus *Sclerotium rolfsii*, or its related fungi. These compounds may also be applied to the plants to control Late Blight of Tomatoes and related diseases, as well as the deleterious effect of nematodes. Preferably the alkyls are methyl, ethyl, and n-propyl.

Those compounds of the general formula wherein naphthyl is α-naphthyl, and $R_1$ and $R_2$ are alkyls of from one to five carbon atoms, preferably straight-chained alkyls of from one to three carbon atoms, mentioned herein, may be applied to plants to control Leaf Rust of Wheat, Late Blight of Tomatoes, and Rice Blast Disease and those diseases related to the pathogenic fungi and bacteria causing these diseases. These same compounds may also be used for a preemergence application to control weeds such as yellow foxtail, barnyardgrass, crabgrass, and pigweed. These same compounds may also be used for postemergence application to control weeds such as jimsonweed, wild mustard, or wild buckwheat.

Those compounds of the general formula wherein naphthyl is β-naphthyl, and $R_1$ and $R_2$ are alkyls of up to five carbon atoms mentioned herein, preferably straight chain alkyls of from one to three carbon atoms, may be applied to plants to control the diseases and related diseases of Late Blight of Tomatoes, that is those of the genus Phytophorans. They may also be used for postemergent application to control weeds such as wild mustard and jimsonweed.

While the invention has been described with reference to specific details of certain illustrative embodiments, it is not intended that it shall be limited thereby except insofar as such details appear in the accompanying claims.

I claim:
1. A S-α-naphthyl N-alkylthiolcarbamate of the general formula:

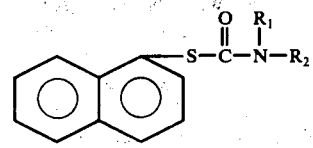

wherein:
$R_1$ is hydrogen, or an alkyl of one to five carbon atoms, and
$R_2$ is an alkyl of one to five carbon atoms.
2. The compound of claim 1, wherein $R_1$ is hydrogen.
3. The compound of claim 2, wherein $R_2$ is a straight chain alkyl of one to five carbon atoms.
4. S-α-naphthyl N-methylthiolcarbamate.
5. The compound of claim 1, wherein $R_1$ is an alkyl of one to five carbon atoms.
6. The compound of claim 5, wherein $R_1$ is a straight chain alkyl of one to five carbon atoms.
7. The compound of claim 6, wherein $R_1$ is methyl.
8. The compound of claim 6, wherein both $R_1$ and $R_2$ are straight chain alkyls of up to five carbon atoms.
9. S-α-naphthyl N,N-dimethylthiolcarbamate.
10. A S-β-naphthyl N-alkylthiolcarbamate of the general formula:

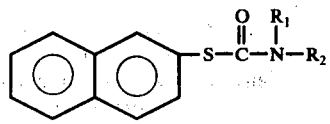

wherein:
$R_1$ is hydrogen, and
$R_2$ is an alkyl of from one to five carbon atoms.
11. The compound of claim 10, wherein $R_2$ is a straight chain alkyl of from one to five carbon atoms.
12. S-β-naphthyl N-methylthiolcarbamate.

* * * * *